United States Patent [19]
Agosta

[11] 4,037,274
[45] July 26, 1977

[54] APPLIANCE AND METHOD FOR FACILITATING HAIRPIECE ATTACHMENT

[76] Inventor: Frank L. Agosta, 26061 Fernwood, Roseville, Mich. 48066

[21] Appl. No.: 607,345

[22] Filed: Aug. 25, 1975

[51] Int. Cl.² .................. A61F 1/00; A61B 17/00; A61L 17/00
[52] U.S. Cl. .......................................... 3/1; 128/330; 128/335.5
[58] Field of Search ................................ 132/53; 3/1

[56] References Cited

U.S. PATENT DOCUMENTS

| | | | |
|---|---|---|---|
| 1,490,479 | 4/1924 | Noel | 132/53 |
| 3,608,095 | 9/1971 | Barry | 3/1 |
| 3,621,837 | 11/1971 | Gindes | 3/1 |
| 3,858,245 | 1/1975 | Náte | 3/1 |
| 3,858,247 | 1/1975 | Bauman | 3/1 |

*Primary Examiner*—Channing L. Pace
*Attorney, Agent, or Firm*—Arnold S. Weintraub

[57] ABSTRACT

An appliance for facilitating hair piece attachment includes a snap member. The snap member has a suture attached thereto and which is surgically inserted into the user's scalp to secure the snap thereonto. A surgical needle is, optionally, secured to the suture.

5 Claims, 4 Drawing Figures

APPLIANCE AND METHOD FOR FACILITATING HAIRPIECE ATTACHMENT

BACKGROUND OF THE INVENTION

1. Field of the Invention

The present invention pertains to hairpieces. More particularly, the present invention pertains to means for facilitating the attachment of hairpieces. Even more particularly, the present invention concerns means and methods for facilitating the attachment of hairpieces to the user's scalp.

2. Prior Art

Modern day clothing styles and promotions, when coupled with modern day hair styles, have dictated a trend away from the appearance of being bald. Thus, there has been a proliferation of means and methods for giving the appearance of having a "full" head of hair.

For example, men's hairpieces and wigs are not widely employed. However, there is a drawback in their usage due to the necessity of tapes and the like. Furthermore, such hair pieces can not be worn in a shower, when swimming, and in other environments. Further, wigs have a tendency to shift, fall off and the like. Therefore, the prior art has sought other alternatives. One such example is a hair transplant. However, a hair transplant is costly and its success is dependent upon the health of the person, i.e. a transplant cannot be successfully performed on a diabetic.

Another recent development has been the implantation, into a user's scalp, of means for facilitating the attachment of a hairpiece to the scalp. For example, in U.S. Pat. No. 3,755,824, there is disclosed a looped suture of polypropylene which is implanted in the user's scalp and wherein the loop is disposed exteriorly of the scalp. A hairpiece is then tied or otherwise secured to the loops. This arrangement, however, provides entanglements and other discomfitures.

In U.S. Pat. No. 3,553,737 there is taught the embedding of a suture in the scalp. The suture is a continuous member, having portions thereof disposed above the surface of the scalp. The suture is placed around the scalp and is tied to itself to form a continuous loop. A gridwork of the type having hair secured thereto is then woven to the anchor points defined by the continuous suture. This method renders detachment of the hair piece very difficult.

The present invention, on the other hand, provides an improvement over the latter two methods discussed above.

SUMMARY OF THE INVENTION

In accordance with the present invention there is provided an appliance for facilitating the attachment of a hairpiece. The appliance hereof comprises a male snap member having a suture secured thereto. The suture is a monofilament member for hygienic purposes. Preferably, the suture comprises a monofilament of silver, sterling silver or stainless steel.

The present appliance is utilized by securing the male snap member to the user's scalp. This is achieved by surgically inserting one end of the suture into the scalp at a first point, withdrawing the suture from the scalp at a second point and tying the one end of the suture to the other end thereof.

Optionally, a cap or clamp can be placed over the junction of the two ends of the suture.

Furthermore, a surgical needle can be secured to the one end of the suture which is drawn through the scalp.

According to the present invention, a hairpiece is attached to the scalp by securing to the hairpiece backing, a plurality of female snap members. The female snap members are disposed on the backing in a predetermined fashion such that they are coincident with the male snap members when the hairpiece is properly positioned. Thus, by snapping the male and female members together the hairpiece is securely attached.

For a more comprehensive discussion of the present invention, reference is made to the following detailed description and accompanying drawing. In the drawing, like reference characters refer to like parts throughout the several views in which:

DESCRIPTION OF THE PREFERRED EMBODIMENT

Figure 1:
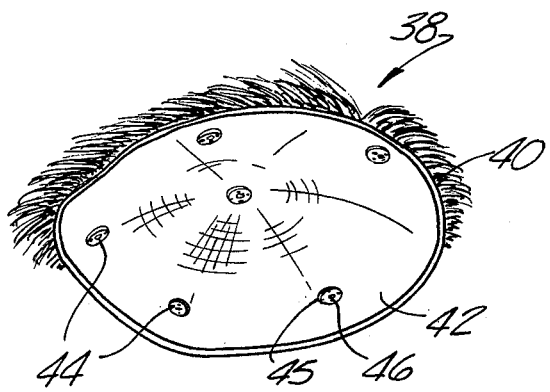
FIG. 1 is a top plan view of a scalp having the appliance of the present invention secured thereto.
Figure 2:
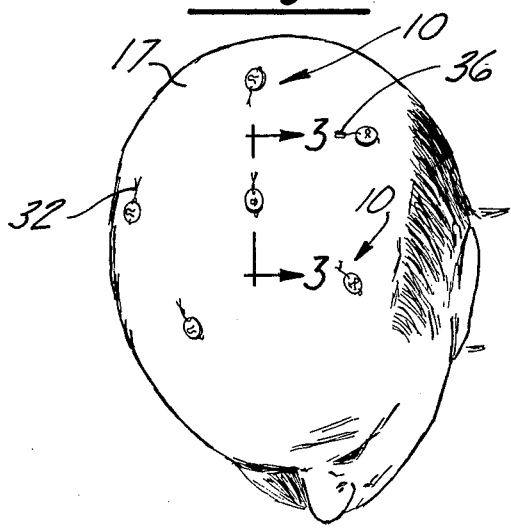
FIG. 2 is a perspective view of a hairpiece having the female snap members secured thereto.

Now, with reference to the drawing, there is depicted therein the appliance of the present invention, generally indicated at 10, and the usage thereof.

The appliance 10 comprises a male snap member 12 having a base 14 and an upstanding central projection 16. The base 14 is adapted to seat on the scalp 17 of a person and the projection receives a complementary or female snap member, in a manner to be described subsequently.

The appliance 10 further comprises an elongated suture 18 having free ends 20 and 22. The suture 18 is secured to the base 14 by any suitable means such as by soldering or the like. Alternatively, the suture can comprise two separate members, each having one end thereof secured to the base in the manner heretofore described. The suture 18 can be formed from any suitable material which is amenable to implantation or emplacement within the scalp of a person. For hygienic and surgical reasons, therefore, the suture must be formed from a monofilament. Suitable materials for use as a suture herein include, for example, polypropylene, silver, sterling silver and stainless steel monofilaments. Preferably, the suture 18 is either sterling silver or stainless steel. These two materials have been found to be the most resistant to bacteriological contamination and/or infection as well as being easily surgically implanted.

Referring again to the drawing, the appliance 10 may also, include a surgical needle 24. The needle 24 is secured to the suture 18 at one end thereof, 20 or 22. The needle 24 includes a hook portion 26 and a connecting element 28 having an aperture 29 formed therethrough. The needle is secured to the suture 18 by inserting the end 20 or 22 through the aperture 29, and then wrapping the end 20 or 22 around itself.

Figure 3:
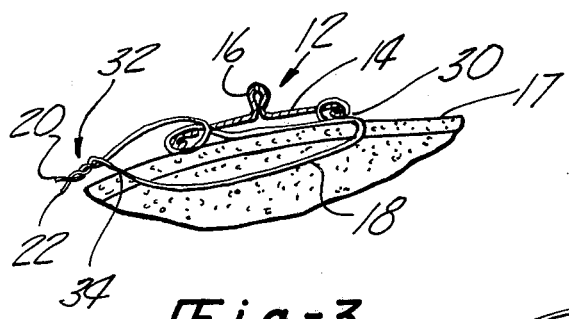
FIG. 3 is a cross-sectional view taken along the line 3—3 of FIG. 1.
Figure 4:
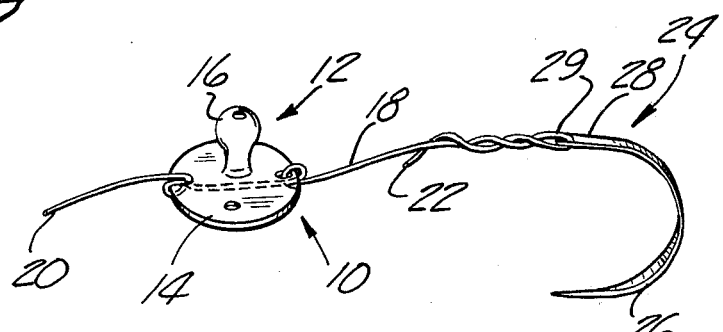
FIG. 4 is a perspective view of the appliance hereof.

As shown in FIG. 3, the appliance 10 is deployed by inserting one end 20 or 22 of the suture 18 at a first point 30 in the scalp 17 of a person. The inserted end of the suture is then withdrawn at a second point 34 of the scalp 17. Where the appliance includes the needle 24, the end 20 or 22 carrying the needle 24 defines the inserted end. By inserting or implanting the suture in the scalp, the male snap member 12 is fixed in position on the scalp of the person.

After withdrawing the suture from the scalp the inserted end is then coiled about the other end of the suture to define a junction 32 and to fix the suture in position. Where the surgical needle is employed, the needle is first removed, by any suitable means, from the suture end associated therewith, and then the coiling is effected.

After the two ends 20, 22 are joined, a cap 36 may be used to enshroud the junction. The cap prevents any irritation to the scalp caused by the rubbing of the junction thereagainst. The cap can be formed of any suitable non-toxic material.

As noted hereinbefore, the present appliance is used to facilitate the securement or attachment of a pairpiece to the scalp of a person. Thus, and in accordance herewith, in practicing the present invention, and as depicted in FIG. 1, a plurality of appliances 10 are strategically affixed to the scalp 17 of a person in the manner heretofore described.

In attaching a hairpiece to a person's scalp, as contemplated by the present invention, there is provided a hairpiece 38. The hairpiece 38 comprises a plurality of strands or tufts of hair 40. The hair 40 is secured to a backing, such as a net 42. Also, secured to the backing is a plurality of complementary or female snap members 44. The female snap members 44 each include a base 45 and a recess 46 which is adapted to securely releasably receive the projection 16 of an associated male snap member 12. The female snap members 44 are secured to the backing 42 such that upon proper positioning of the hairpiece on the head of the user they are coincident with the male snap members. To attach the hairpiece to the user's head, the coincident male and female snap members are manually snapped together.

To remove the hairpiece the snap members are easily separated by manual manipulation.

It is apparent from the preceding that there has been described an appliance which facilitates the attachment and removal of a hairpiece from the head of a user.

Having, thus, described the invention, what is claimed is:

1. An appliance for facilitating the attachment of a hairpiece to the scalp of a person, comprising:
   a. a snap member, the snap member comprising a base and an upstanding projection,
   b. an elongated suture having a first end and a second end, the suture being connected to the snap member medially of the suture, and
   c. a surgical needle connected to the suture at the first end thereof, the needle comprising a hook element and a connecting element integrally formed therewith, the connecting element being detachably connected to the first end of the suture, and
   wherein the first end of the suture is adapted to be inserted into the scalp via the needle beneath the snap member and exited from the scalp proximate the second end of the suture such that the two ends of the suture are interconnectable to render the snap member detachably connected to the scalp.

2. The appliance of claim 1 wherein the suture is a monofilament member.

3. The appliance of claim 2 wherein the monofilament is formed from a material selected from the group consisting of silver, alloys of silver, ferrous metal alloys, and polypropylene.

4. The appliance of claim 1 which further comprises: means for enshrouding the ends of the suture after the joining thereof.

5. A method for detachably connecting a hairpiece to the head of a person, comprising:
   a. placing on the scalp at a predetermined position an appliance comprising:
      1. a snap member having a base and an upstanding projection,
      2. an elongated suture having a first end and a second end, the snap member being mounted to the suture medially thereof, and
      3. a surgical needle, the first end of the suture being detachably connected to the needle,
   b. inserting the needle into the scalp at a first point,
   c. drawing the needle through the scalp beneath the snap member,
   d. withdrawing the needle from the scalp at a second point thereof proximate the second end of the suture, such that the first end of the suture is drawn through the scalp beneath the snap member and is withdrawn from the scalp proximate the second end of the suture,
   e. detaching the needle from the first end of the suture,
   f. joining together the first and second ends of the suture above the scalp,
   g. securing to a hairpiece a snap member having a recess for receiving the projection, and
   h. snapping the projection into the recess.

* * * * *